US012724031B2

(12) United States Patent
Petropoulos et al.

(10) Patent No.: US 12,724,031 B2
(45) Date of Patent: Sep. 1, 2026

(54) METHODS FOR MODULATION OF CORONAVIRUS INFECTION

(71) Applicant: Laboratory Corporation of America Holdings, Burlington, NC (US)

(72) Inventors: Christos J. Petropoulos, Half Moon Bay, CA (US); Danielle Ditirro, Walnut Creek, CA (US); Mary T. Wrin, Fremont, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 562 days.

(21) Appl. No.: 18/252,680

(22) PCT Filed: Nov. 11, 2021

(86) PCT No.: PCT/US2021/058935
§ 371 (c)(1),
(2) Date: May 11, 2023

(87) PCT Pub. No.: WO2022/103933
PCT Pub. Date: May 19, 2022

(65) Prior Publication Data
US 2024/0011992 A1 Jan. 11, 2024

Related U.S. Application Data

(60) Provisional application No. 63/112,290, filed on Nov. 11, 2020.

(51) Int. Cl.
*G01N 33/569* (2006.01)
*G01N 33/50* (2006.01)

(52) U.S. Cl.
CPC ... *G01N 33/56983* (2013.01); *G01N 33/5091* (2013.01); *G01N 2333/165* (2013.01); *G01N 2333/705* (2013.01); *G01N 2469/20* (2013.01); *G01N 2500/10* (2013.01)

(58) Field of Classification Search
CPC ....... G01N 2333/165; G01N 2333/705; G01N 2469/20; G01N 2500/10; G01N 33/5091; G01N 33/56983
See application file for complete search history.

(56) References Cited

PUBLICATIONS

Lei et al. Nature Communications, published on Apr. 24, 2020, Issue 11, No. 2070, pp. 1-5.*

Wu et al. Proc Natl Acad Sci U S A. Nov. 9, 2009;106(47):19970-19974.*

Crawford et al. (Viruses, published on May 6, 2020, vol. 12 (5): 513. Doi: . 10.3390/v12050513.*

Schmidt et al. JEM, published on Jul. 1, 2020 217 (11): e20201181. doi: 10.1084/jem.20201181.*

Lei et al. Nature Communications, published on Apr. 24, 2020, vol. 11, No. 2070 pp. 1-5.*

Chen et al. JID, 2017, vol. 251, pp. 1807-1815.*

Papapostolou et al. Cells, 2023, vol. 12 (5). pp. 1-22.*

Duan et al. PNAS, Apr. 6, 2020, 117 (17) , pp. 9490-9496.*

PCT/US2021/058935, "International Search Report and Written Opinion," Apr. 20, 2022, 16 pages.

Bosch et al., "The Coronavirus Spike Protein Is a Class I Virus Fusion Protein: Structural and Functional Characterization of the Fusion Core Complex," Journal of Virology, vol. 77(16), Aug. 2003: pp. 8801-8811, <https://www.ncbi.nlm.nih.gov/pmc/articles/PMC167208/>.

Changeux, "The nicotinic acetylcholine receptor: a typical 'allosteric machine'," Phil. Trans. R. Soc. B., vol. 373 (1749), Jun. 19, 2018: pp. 1-12, <https://www.ncbi.nlm.nih.gov/pmc/articles/PMC5941169/>.

Changeux et al., "A nicotinic hypothesis for Covid-19 with preventive and therapeutic implications," C. R. Biologies, vol. 343(1), Jun. 5, 2020: pp. 33-39, >https://comptes-rendus.academie-sciences.fr/biologies/item/CRBIOL_2020__343_1_33_0/>.

Hoffmann, et al., "SARS-CoV-2 Cell Entry Depends on ACE2 and TMPRSS2 and Is Blocked by a Clinically Proven Protease Inhibitor", Cell, vol. 181, No. 2, Mar. 5, 2020, pp. 271-280.

Hu, et al., "Development of Cell-Based Pseudovirus Entry Assay to Identify Potential Viral Entry Inhibitors and Neutralizing Antibodies Against SARS-CoV-2", Genes & Diseases, vol. 7, No. 4 Available Online At : https://www.ncbi.nlm.nih.gov/pmc/articles/PMC7 366953/pdf/main.pdf, Jul. 17, 2020, pp. 551-557.

(Continued)

*Primary Examiner* — Bao Q Li
(74) *Attorney, Agent, or Firm* — Kilpatrick Townsend & Stockton LLP

(57) ABSTRACT

The present disclosure relates to methods, compositions and systems for modulation of a coronavirus (e.g., SARS CoV-2) and/or the evaluation of compounds that can modulate infectivity of the coronavirus. For example, disclosed is a method to identify a compound that can modulate infection by the coronavirus comprising the steps of: expressing an angiotensin-converting enzyme 2 receptor (ACE-2) and/or a nicotinic acetylcholine receptor (nAChR) receptor on a target cell; contacting the target cell with a viral particle comprising at least a portion of the coronavirus spike protein in the absence and the presence of the compound; and measuring levels of infection of the target cell in order to determine infectivity of the viral particle in the presence or absence of the compound. Also, disclosed are compounds and methods of treatment identified using the methods, compositions, and systems.

20 Claims, 4 Drawing Sheets

(56) References Cited

PUBLICATIONS

Oliveira,et al., “A Potential Interaction Between the SARS-CoV-2 Spike Protein and Nicotinic Acetylcholine Receptors”, Biophysical Journal, vol. 120, No. 6, Sep. 14, 2020, pp. 983-993.
Oliveira et al., “Simulations support the interaction of the SARS-CoV-2 spike protein with nicotinic acetylcholine receptors.” bioRxiv, Jul. 17, 2020: pp. 1-15, <https://www.biorxiv.org/content/10.1101/2020.07.16.206680v1>.
Oliveira et al., “Simulations support the interaction of the SARS-CoV-2 spike protein with nicotinic acetylcholine receptors.” bioRxiv, Sep. 14, 2020: pp. 1-14, <https://www.biorxiv.org/content/10.1101/2020.07.16.206680v3>.
Petropoulos et al, “A Novel Phenotypic Drug Susceptibility Assay for Human Immunodeficiency Virus Type 1,” Antimicrob. Agents Chemother., vol. 44(4), Apr. 2000: pp. 920-928, <https://www.ncbi.nlm.nih.gov/pmc/articles/PMC89793/>.
Richman et al., “Rapid evolution of the neutralizing antibody response to HIV type 1 infection,” PNAS, vol. 100(7), Apr. 1, 2003: pp. 4144-4149, <https://www.pnas.org/doi/10.1073/pnas.0630530100>.
Walls et al., “Structure, Function, and Antigenicity of the SARS-CoV-2 Spike Glycoprotein,” Cell, vol. 181(2), Apr. 16, 2020: pp. 281-292.e6, <https://www.sciencedirect.com/science/article/pii/S0092867420302622>.
Walls et al., Correction: “Structure, Function, and Antigenicity of the SARS-CoV-2 Spike Glycoprotein,” Cell, vol. 183 (6), Dec. 10, 2020: p. 1735, <https://www.sciencedirect.com/science/article/pii/S0092867420302622>. (Correction included in the PDF document, Wallsetal, as the last two pages, an update page and p. 1735).
Whitcomb et al., “Development and Characterization of a Novel Single-Cycle Recombinant-Virus Assay To Determine Human Immunodeficiency Virus Type 1 Coreceptor Tropism,” Antimicrob. Agents Chemother., vol. 51(2), Feb. 2007: pp. 1-23, <https://journals.asm.org/doi/full/10.1128/AAC.00853-06>.
EP21820762.9, “Office Action”, dated Oct. 21, 2024, 4 pages.
PCT/US2021/058935, “International Preliminary Report on Patentability”, dated May 25, 2023, 11 pages.
PCT/US2021/058935, “Invitation to Pay Additional Fees and, Where Applicable, Protest Fee”, dated Feb. 25, 2022, 5 pages.
Japanese Application No. 2023-528054, Office Action mailed Dec. 17, 2025, 10 pages.

* cited by examiner

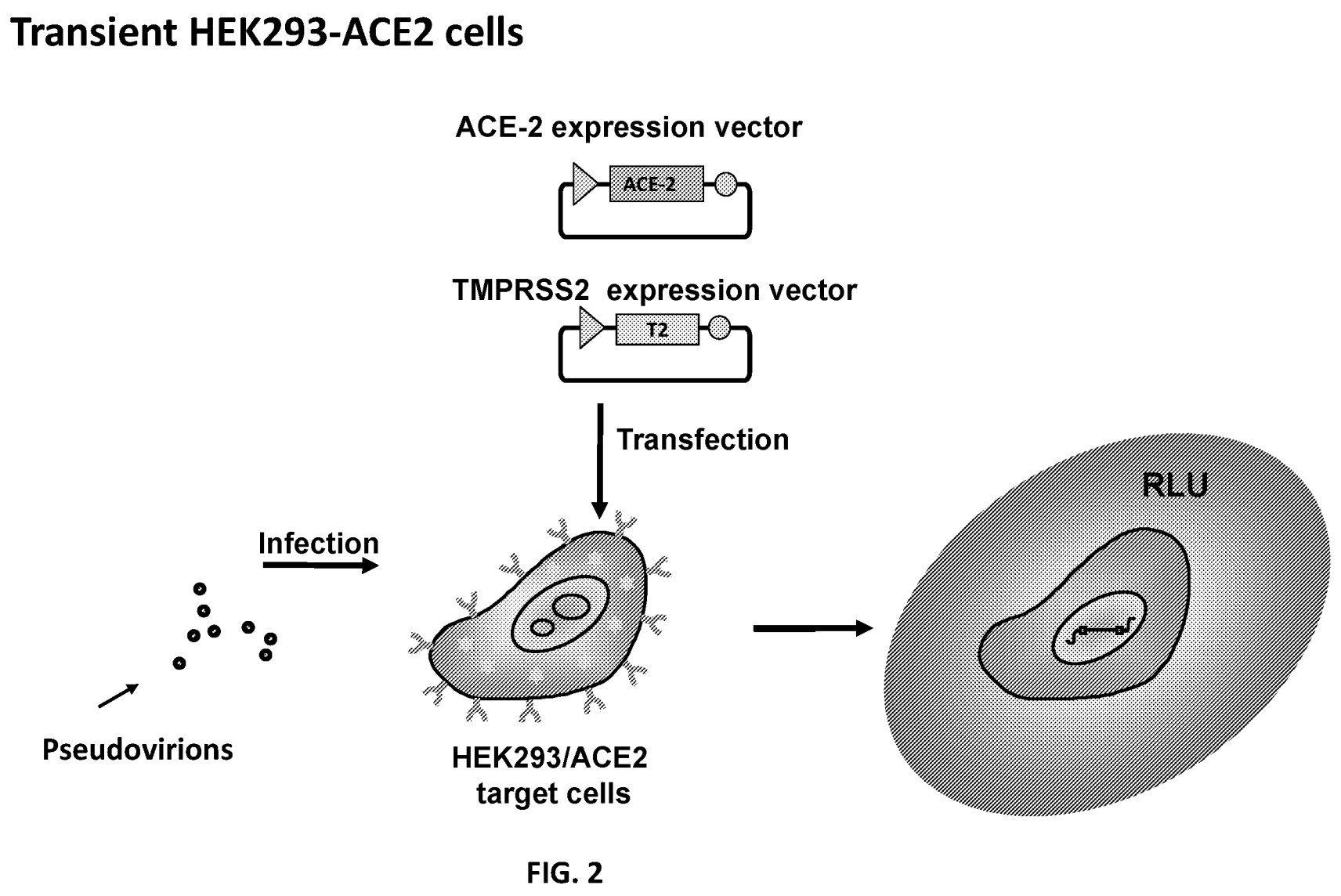

Transient HEK293-ACE2 cells

ACE-2 expression vector

ACE-2

TMPRSS2 expression vector

T2

Transfection

HEK293/ACE2 target cells

RLU

Infection

Pseudovirions

FIG. 2

METHODS FOR MODULATION OF CORONAVIRUS INFECTION

RELATED APPLICATION

This application claims priority to International application number PCT/US2021/058935, filed Nov. 11, 2021, which claims the benefit of U.S. Provisional Application No. 63/112,290, filed Nov. 11, 2020. The disclosure of these applications is incorporated by reference herein in their entireties.

FIELD

The present disclosure relates to methods, compositions, and systems for modulation of a coronavirus, such as SARS CoV-2.

BACKGROUND

The 2019/2020 Severe Acute Respiratory Syndrome coronavirus 2 (SARS CoV-2) outbreak in Wuhan China has provided sobering evidence that regional outbreaks of zoonotic virus infection have the potential to spread rapidly across much larger geographic regions. Given the widespread distribution of infections, SARS CoV-2 may now be established as an endemic virus in the world population. The acute respiratory syndrome caused by SARS CoV-2 was named coronavirus disease 2019 (COVID-19).

The spike (S) protein from SARS-CoV-2 is a fusion protein found on the surface of the virion that mediates entry into host cells. The S protein is an extensively glycosylated homotrimer with each monomer formed by tree domains: head, stalk, and cytoplasmic tail. The head is made up of two subunits: the 51 subunit is responsible for binding to angiotensin converting enzyme 2 (ACE-2) of the host cell, and the S2 subunit is responsible for membrane fusion (Bosch et al., *J. Virol.,* 2003, 77:8801-8811; Walls et al., *Cell,* 2020, 181:281-292.e286).

Recently, given the low prevalence of smokers among hospitalized COVID-19 patients, it was proposed that nicotine may offer some protective value to mitigate COVID-19. Additional studies indicated that the S protein may interact with nicotinic acetylcholine receptors (nAChRs) due to the fact that the S protein from SARS-COV-2 contains a 2018, sequence motif similar to known nAChR antagonists (Changeux, 2018, *Philos. Trans. R. Soc. Land. B. Biol. Sci.,* 373 (1749): 20170174; Oliveira et al., Jul. 17, 2020, bioRxiv. There are three primary types of nAChRs: the $\alpha4\beta2$ nAChR found primarily in brain; the $\alpha\beta\gamma\delta$ nAChR found primarily in muscle, and the $\alpha7$ nAChR found primarily in the CNS and immune cells (Oliveira, 2020). The $\alpha7$ nAChR is a homodimer, whereas the other two nAChRs are heterodimers.

There is a need for treatment methods and therapeutic agents that can modulate and reduce symptoms of viral infections, such as infections with SARS-CoV-2. Also, there is a need for methods that can assay the efficacy of potential therapeutic agents for coronavirus infections, such as infections with SARS-CoV-2.

SUMMARY

The present disclosure related to methods, compositions, and systems for modulation of coronavirus such as SARS CoV-2. The disclosed methods, compositions, and systems may be embodied in a variety of ways. For example, in one embodiment disclosed is a method to identify a compound that can modulate infection by SARS CoV-2 comprising the steps of: expressing an angiotensin-converting enzyme 2 receptor (ACE-2) and/or a nicotinic acetylcholine receptor (nAChR) receptor on a target cell; contacting the target cell with a viral particle comprising at least a portion of the SARS CoV-2 spike protein in the absence and the presence of the compound; and measuring levels of infection of the target cell in order to determine infectivity of the viral particle in the presence or absence of the compound. Also disclosed are systems, compositions, and computer-program products tangibly embodied in a non-transitory machine-readable storage medium, including instructions configured to perform any of the steps of the methods or run any part of the systems.

BRIEF DESCRIPTION OF THE DRAWINGS

The disclosure may be better understood by referencing the following non-limiting drawings.

FIG. 2 depicts an example of in vitro target cells transfected with a SARS CoV and SARS CoV-2 ACE-2 expression vector and a human airway transmembrane trypsin-like serine protease (TMPRSS2) expression vector used to detect SARS-CoV-2 infection in accordance with an embodiment of the disclosure.

DETAILED DESCRIPTION

Figure 1:
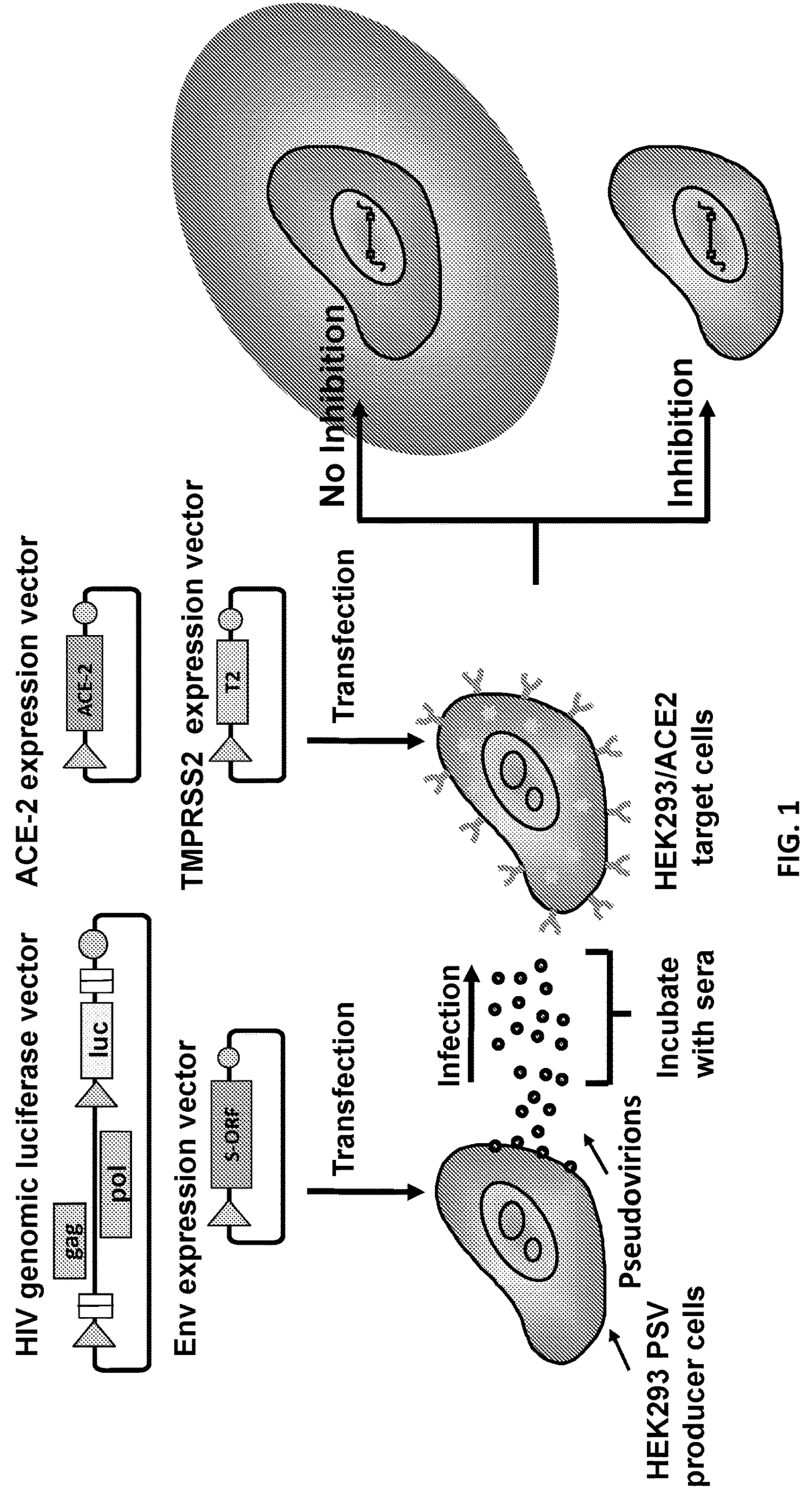
FIG. 1 depicts an exemplary assay to detect SARS-CoV-2 neutralizing antibodies in accordance with an embodiment of the disclosure. PSV refers to pseudovirus; S-ORF refers to the Coronavirus S protein (envelope spike) open reading frame; ACE-2 refers to the SARS CoV and SARS CoV-2 receptor (angiotensin converting enzyme 2); and TMPRSS2 refers to the human airway transmembrane trypsin-like serine protease. Pseudovirions are shown as particles emanating from producer cells.

The following description recites various aspects and embodiments of the present compositions and methods. No particular embodiment is intended to define the scope of the compositions and methods. Rather, the embodiments merely provide non-limiting examples of various methods and systems that are at least included within the scope of the compositions and methods. The description is to be read from the perspective of one of ordinary skill in the art; therefore, information well known to the skilled artisan is not necessarily included.

Definitions

The present disclosure now will be described more fully hereinafter. The disclosure may be embodied in many different forms and should not be construed as limited to the aspects set forth herein; rather, these aspects are provided so that this disclosure will satisfy applicable legal requirements. Unless defined otherwise, all technical and scientific terms used herein have the same meaning as is commonly understood by one of ordinary skill in the art to which this disclosure belongs. All patents, applications, published applications, and other publications referred to herein are incorporated by reference in their entireties. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

When introducing elements of the present disclosure or the embodiment(s) thereof, the articles "a," "an," "the," and "said" are intended to mean that there are one or more of the elements. The terms "comprising," "including," and "having" are intended to be inclusive and mean that there may be additional elements other than the listed elements. It is understood that aspects and embodiments of the disclosure described herein include "consisting" and/or "consisting essentially of" aspects and embodiments.

The term "and/or," when used in a list of two or more items, means that any one of the listed items can be employed by itself or in combination with any one or more of the listed items. For example, the expression "A and/or B" is intended to mean either or both of A and B, i.e. A alone, B alone, or A and B in combination. The expression "A, B, and/or C" is intended to mean A alone, B alone, C alone, A and B in combination, A and C in combination, B and C in combination, or A, B, and C in combination.

Various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

The methods and systems of the disclosure may be applied to a variety of sample types. In certain embodiments, the sample comprises a biological sample. In some embodiments, the biological sample is taken from a subject. In some embodiments, the subject may be a human subject. In some embodiments of the method, the subject may be suspected to have been exposed to any pathogen of interest. In certain embodiments, the pathogen is SARS-CoV-2. As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse or sheep) and a primate (e.g., a monkey, such as a cynomolgus monkey, gorilla, chimpanzee, or a human).

"Sample" or "patient sample" or "biological sample" or "specimen" are used interchangeably herein. The source of the sample may be solid tissue as from a fresh tissue, frozen and/or preserved organ or tissue or biopsy or aspirate. The source of the sample may be a liquid sample. Non-limiting examples of liquid samples include cell-free nucleic acid, blood or a blood product (e.g., serum, plasma, or the like), urine, nasal swabs, biopsy sample (e.g., liquid biopsy) or combinations thereof. The term "blood" encompasses whole blood, blood product or any fraction of blood, such as serum, plasma, buffy coat, or the like as conventionally defined. For example, in certain embodiments (e.g., COVID-19) the biological sample comprises a specimen from either the upper or lower respiratory system. In an embodiment, the sample may comprise, e.g., at least one of a nasopharyngeal swab, a mid-turbinate swab, anterior nares swab, an oropharyngeal swab, sputum, a lower respiratory tract aspirate, a bronchoalveolar lavage, a nasopharyngeal wash and/or aspirate or a nasal aspirate. The sample may contain compounds that are not naturally intermixed with the tissue in nature such as preservatives, anticoagulants, buffers, fixatives, nutrients, antibiotics, or the like.

"Treatment" and other forms of this word refer to the administration of an agent to impede a disease or its symptoms. Treatment may also refer to any course which one skilled, for example, a treating physician, deems expedient.

Methods for Detection of a Compound that Modulates SARS Infectivity

In one embodiment is a method to identify a compound that can modulate infection by a coronavirus comprising: expressing an angiotensin-converting enzyme 2 receptor (ACE-2) and/or a nicotinic acetylcholine receptor (nAChR) receptor on a target cell; contacting the target cell with a viral particle comprising at least a portion of the spike protein in the absence and the presence of the compound; and measuring levels of infection of the target cell in order to determine infectivity of the viral particle in the presence or absence of the compound. In some aspects, the coronavirus is SARS CoV-2. There are numerous variants of SARS CoV-2. In some embodiments, the SARS CoV-2 is a variant, and the variant is the Delta variant, Alpha variant, Beta variant, Gamma variant, Epsilon variant, Eta variant, Iota variant, Kappa variant, 1.617.3 variant, Mu variant, or Zeta variant. In some embodiments, the variant is the Delta variant. In other aspects, the coronavirus is SARS CoV or seasonal human coronavirus NL63.

In certain embodiments of these methods, the viral particle is an HIV pseudovirion. For example, in one embodiment, the method may utilize the PhenoSense® (PS) CoV neutralizing antibody (nAb) Assay format as disclosed herein. Or the assay may utilize the PhenoSense® CoV Assay, but replacing the neutralizing antibody (or subject e.g., a patient, sera) with a compound to be evaluated for antiviral activity. Also, in certain embodiments, the nAChR is the $\alpha7$ nAChR.

Thus, additionally and/or alternatively disclosed is a method to identify a compound that can modulate SARS CoV-2 infection, comprising:

(a) transfecting into a producer cell:
  i) a nucleic acid encoding a SARS CoV-2 spike protein or a portion thereof, and
  ii) a genomic viral expression vector comprising sequences from a second virus that is not a coronavirus and that comprises an indicator nucleic acid that produces a detectable signal;
(b) incubating the transfected producer cell under conditions such that pseudovirions that comprise the SARS CoV-2 spike protein or a portion thereof are generated;
(c) contacting the pseudovirions of step (b) with a target cell under conditions such that the pseudovirions infect the target cell and in the presence or absence of the compound, wherein the target cell expresses an angiotensin-converting enzyme 2 receptor (ACE-2) and/or a nicotinic acetylcholine receptor (nAChR); and (d) measuring the amount of the detectable signal produced by the target cell in order to determine infectivity of the viral particles in the presence or absence of the compound.

In some embodiments, the SARS CoV-2 is a variant, and the variant is the Delta variant, Alpha variant, Beta variant, Gamma variant, Epsilon variant, Eta variant, Iota variant, Kappa variant, 1.617.3 variant, Mu variant, or Zeta variant. In some embodiments, the variant is the Delta variant.

In other aspects of these methods, the methods are used to identify a compound that can modulate infection by another coronavirus, such as SARS CoV or seasonal human coronavirus NL63. In these aspects, the nucleic acid in step (a)(i) instead encodes the spike protein or a portion thereof from SARS CoV or seasonal human coronavirus NL63.

In certain embodiments, the second virus is a human immunodeficiency virus (HIV) or a genetically modified HIV. For example, the HIV may be modified to remove genomic sequences that encode the HIV envelope protein. Also in certain embodiments, the nAChR is the α7 nAChR.

In yet other embodiments, disclosed is a method to determine the efficacy of a compound to modulate the production of SARS CoV-2 neutralizing antibodies in a subject, comprising:

(a) expressing an angiotensin-converting enzyme 2 receptor (ACE-2) and/or a nicotinic acetylcholine receptor (nAChR) receptor on a target cell;

(b) contacting the target cell with a viral particle comprising at least a portion of the SARS CoV-2 spike protein, optionally from the subject, in the absence and the presence of: (i) a first sample obtained from the subject before treatment with the compound, and (ii) a second sample obtained from the subject after treatment with the compound, wherein the first and second samples contain antibodies; and (c) measuring levels of infection of the target cell in order to determine infectivity of the viral particles in the presence of the first subject sample or the second subject sample in order to determine a change in the activity or amount of neutralizing antibodies in the subject's first and second samples, wherein a change in the activity or amount of neutralizing antibodies present in the samples is detected as a change in infectivity of the viral particles.

In some embodiments, the SARS CoV-2 is a variant, and the variant is the Delta variant, Alpha variant, Beta variant, Gamma variant, Epsilon variant, Eta variant, Iota variant, Kappa variant, 1.617.3 variant, Mu variant, or Zeta variant. In some embodiments, the variant is the Delta variant.

In other aspects of these methods, the methods are used to determine the efficacy of a compound to modulate the production of neutralizing antibodies for another coronavirus, such as SARS CoV or seasonal human coronavirus NL63. In these aspects, the viral particle in step (b) comprises at least a portion of the spike protein from SARS CoV or seasonal human coronavirus NL63.

In an embodiment, the viral particle is an HIV pseudovirion. For example, the HIV may be modified to remove genomic sequences that encode the HIV envelope protein. Also, in certain embodiments, the nAChR is the α7 nAChR.

In yet another embodiment, disclosed is a method to determine the efficacy of a compound to modulate the production of SARS CoV-2 neutralizing antibodies in a subject, comprising:

(a) transfecting into a PSV producer cell:

i) a nucleic acid encoding a SARS CoV-2 spike protein or a portion thereof from the subject, and ii) a genomic viral expression vector comprising sequences from a second virus that is not a coronavirus and that comprises an indicator nucleic acid that produces a detectable signal;

(b) incubating the transfected producer cells under conditions such that the producer cells produce pseudovirions that comprise the SARS CoV-2 spike protein or a portion thereof;

(c) contacting the pseudovirions of step (b) with a target cell in the presence or absence of: (i) a first sample obtained from the subject before treatment with the compound, and (ii) a second sample obtained from the subject after treatment with the compound, wherein the first and second samples contain antibodies, and wherein the target cell expresses an angiotensin-converting enzyme 2 receptor (ACE-2) and/or a nicotinic acetylcholine receptor (nAChR) under conditions such that the pseudovirions infect the target cell;

(d) measuring the amount of the detectable signal produced by the target cell in the presence of the first subject sample and the second subject sample in order to determine a change in the activity or amount of neutralizing antibodies in the subject's first and second samples, wherein a change in the activity or amount of neutralizing antibodies is detected as a change in infectivity of the viral particles.

In some embodiments, the SARS CoV-2 is a variant, and the variant is the Delta variant, Alpha variant, Beta variant, Gamma variant, Epsilon variant, Eta variant, Iota variant, Kappa variant, 1.617.3 variant, Mu variant, or Zeta variant. In some embodiments, the variant is the Delta variant.

In other aspects of these methods, the methods are used to determine the efficacy of a compound to modulate the production of neutralizing antibodies for another coronavirus, such as SARS CoV or seasonal human coronavirus NL63. In these aspects, the nucleic acid in step (a)(i) encodes comprises a spike protein or portion thereof from SARS CoV or seasonal human coronavirus NL63 from the subject.

In certain embodiments, the second virus is HIV or a genetically modified HIV. For example, the HIV may be modified to remove genomic sequences that encode the HIV envelope protein. Also in certain embodiments, the nAChR is the α7 nAChR.

Compositions for Detection of a Compound that Modulate Coronavirus Infectivity

Also disclosed are compositions and systems for the detection of a compound that can modulate coronavirus infectivity, such as infectivity by SARS CoV-2, SARS CoV, or NL63. In some embodiments, the SARS CoV-2 is a variant, and the variant is the Delta variant, Alpha variant, Beta variant, Gamma variant, Epsilon variant, Eta variant, Iota variant, Kappa variant, 1.617.3 variant, Mu variant, or Zeta variant. In some embodiments, the variant is the Delta variant.

In one embodiment, the composition may comprise cells that have been engineered to be either producer cells or target cells as disclosed herein. For example, the system may comprise a first cell (or cells) that has been genetically modified to be a target cell that expresses an angiotensin-converting enzyme 2 receptor (ACE-2) and/or a nicotinic acetylcholine receptor (nAChR) receptor. In an embodiment, the target cell may be genetically modified to also express human airway transmembrane trypsin-like serine protease (TMPRSS2).

Additionally and/or alternatively, the composition may comprise a producer cell (or cells). In certain embodiments, the producer cell may be a genetically modified second cell made by the steps of: transfecting into a the second cell: i) a nucleic acid encoding a SARS CoV-2 spike protein or a portion thereof, and ii) a genomic viral expression vector comprising sequences from a second virus that is not a coronavirus and that optionally comprises an indicator nucleic acid that produces a detectable signal. In an embodiment, the coronavirus spike protein is a coronavirus S protein. In some embodiments, the SARS CoV-2 is a variant, and the variant is the Delta variant, Alpha variant, Beta variant, Gamma variant, Epsilon variant, Eta variant, Iota variant, Kappa variant, 1.617.3 variant, Mu variant, or Zeta variant. In some embodiments, the variant is the Delta variant. In other aspects of these producer cells, the nucleic acid in (i) encodes the spike protein or a portion thereof from SARS CoV or seasonal human coronavirus NL63.

In certain embodiments, the second virus is HIV or a genetically modified HIV. For example, the HIV may be modified to remove genomic sequences that encode the HIV envelope protein. Also in certain embodiments, the nAChR is the α7 nAChR. Or other nAChRs may be used. Also, in some embodiments, the target cell further expresses human airway transmembrane trypsin-like serine protease (TMPRSS2).

A variety of constructs may be used as an indicator nucleic acid. In certain embodiments, the indicator nucleic acid comprises an indicator gene. For example, the indicator gene may be a luciferase gene.

In certain embodiments, the S protein is from a subject infected with a coronavirus. In certain embodiments, the subject is infected with severe acute respiratory syndrome coronavirus 2 (SARS-CoV-2). In some embodiments, the SARS CoV-2 is a variant, and the variant is the Delta variant, Alpha variant, Beta variant, Gamma variant, Epsilon variant, Eta variant, Iota variant, Kappa variant, 1.617.3 variant, Mu variant, or Zeta variant. In some embodiments, the variant is the Delta variant. In other embodiments, the subject is infected with SARS CoV or NL63.

A variety of cells may be used to generate the target cell or the producer cell. In certain embodiments, the producer cells and/or the target cells are mammalian cells. Also, in some embodiments, the producer cells and/or the target cells are human cells. In some cases the producer cells and/or the target cells are human embryonic kidney (HEK) cells, as for example 293 HEK cells.

Systems for Detection of Compounds that can Modulate Coronavirus

Also disclosed are systems for performing any of the steps of the disclosed methods and/or using any of the disclosed compositions and computer-implemented instructions for performing any of the steps of the disclosed methods, and/or using any of the disclosed compositions, or running any of the parts of the disclosed systems.

Thus the system may comprise cells that have been engineered to be either producer cells or target cells as disclosed herein. For example, the system may comprise a target cell (or cells) that has been engineered to express an angiotensin-converting enzyme 2 receptor (ACE-2) and/or a nicotinic acetylcholine receptor (nAChR) receptor. The system may further comprise a station and/or component for contacting the target cell with a viral particle comprising at least a portion of the SARS CoV-2 spike protein in the absence and the presence of a compound to be tested as a potential modulator of SARS CoV-2 infectivity. In one embodiment, the compound may be a subject or a patient sample believed to contain neutralizing antibodies. Additionally, the system may comprise a station and/or component for measuring levels of infection of the target cell in order to determine infectivity of the viral particle in the presence or absence of the compound. In one embodiment, infected cells may comprise a detectable marker. For example, in one embodiment, the target cells may comprise luciferase. Or, the viral particle may comprise luciferase. Thus, in certain embodiments, the system may comprise a station for measuring signal from luciferase due to infection of the target cells. In some embodiments, the SARS CoV-2 is a variant, and the variant is the Delta variant, Alpha variant, Beta variant, Gamma variant, Epsilon variant, Eta variant, Iota variant, Kappa variant, 1.617.3 variant, Mu variant, or Zeta variant. In some embodiments, the variant is the Delta variant. In other embodiments, the viral particle comprises at least a portion of the spike protein of SARS CoV or NL63 instead of SARS CoV-2.

As disclosed herein, in certain embodiments, the viral particle is an HIV pseudovirion. For example, in one embodiment, the method may utilize the PhenoSense® (PS) CoV neutralizing antibody (nAb) Assay format as disclosed herein. Or the assay may utilize the PhenoSense® CoV Assay, but replacing the neutralizing antibody (or subject e.g., patient, sera) with a compound to be evaluated for antiviral activity. Also, in certain embodiments, the nAChR is the α7 nAChR.

Thus, a system may, in certain embodiments, comprise a genetically modified producer cell (or cells). In certain embodiments, the producer cell may be made by the steps of: transfecting into a producer cell: i) a nucleic acid encoding a SARS CoV-2 spike protein or a portion thereof (or alternatively, a spike protein or portion thereof from SARS CoV or NL63), and ii) a genomic viral expression vector comprising sequences from a second virus that is not a coronavirus and that comprises an indicator nucleic acid that produces a detectable signal. The system may further comprise a station and/or component for incubating the producer cell under conditions such that pseudovirions that comprise the SARS CoV-2 spike protein or a portion thereof (or alternatively, a spike protein or portion thereof from SARS CoV or NL63) are generated. Also, the system may comprise a station and/or component for contacting the pseudovirions made by the producer cell with a target cell under conditions such that the pseudovirions infect the target cell and in the presence or absence of a compound to be tested as a potential modulator of the coronavirus infectivity. In one embodiment, the compound may be a subject or patient sample believed to contain neutralizing antibodies. In certain embodiments, the target cell expresses an angiotensin-converting enzyme 2 receptor (ACE-2) and/or a nicotinic acetylcholine receptor (nAChR). Additionally, the system may comprise a station for measuring levels of infection of the target cell in order to determine infectivity of the viral particle in the presence or absence of the compound. In one embodiment, infected cells may comprise a detectable marker. For example, in one embodiment, the target cells may comprise luciferase. Or, the viral particle may comprise luciferase. Thus, in certain embodiments, the system may comprise a station for measuring signal from luciferase due to infection of the target cells.

In some embodiments, the system or any of the stations of the system, further comprises a computer and/or a data processor. In certain embodiments, the system may comprise one or more computers, and/or a computer product tangibly embodied in a non-transitory computer readable storage medium containing instructions which, when executed on the one or more data processors, cause the one or more data processors to perform actions for performing the methods or implementing the systems of any of embodiments disclosed herein. One or more embodiments described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines. For example, as disclosed below, the system may comprise a computer and/or computer-program product tangibly embodied in a non-transitory machine-readable storage medium for relating changes in infectivity of the viral particles or pseudovirions. Thus, in certain embodiments, the system may comprise components to quantify the measurement. Also, the system may comprise components to perform statistical analysis of the data.

Also disclosed is a computer-program product tangibly embodied in a non-transitory machine-readable storage medium, including instructions configured to run the systems and/or perform a step or steps of the methods of any of the disclosed embodiments. In one embodiment, the system comprises a computer-program product tangibly embodied in a non-transitory machine-readable storage medium, including instructions configured to determine changes in coronavirus (e.g., SARS CoV-2) infectivity caused by a compound of interest. Additionally and/or alternatively, the computer program product may comprise instructions for determining changes in neutralizing antibody response due to treatment with a compound of interest.

EXAMPLES

Example 1—Detection of SARS CoV-2 Neutralizing Antibodies

The pathogenicity of SARS CoV-2 necessitates that all cell-based in vitro studies involving live (i.e. replication competent) virus are performed under BSL3 containment, including assessments of nAb activity. The assay as disclosed herein provides an accurate, reproducible, and high-throughput alternative that can be conducted under BSL2 containment resulting in reduced risk to laboratory personnel and lower costs to vaccine sponsors and providers of convalescent sera.

Such an assay allows for studies to establish protective immunity levels to SARS CoV-2 and would contributes to predicting individual prognoses and monitoring recovery following an infection with the pathogen. Additionally, the assay can be used to study vaccine and treatment responses and to assist in the selection of donor plasma for convalescent plasma therapy.

Presently available assays are insufficient for these applications.

The PS CoV nAb Assay has been developed by leveraging the proprietary PhenoSense® Assay platform that was developed to evaluate antiretroviral drug susceptibility (Petropoulos et al., AAC 2000) and later adapted to evaluate entry inhibitors, nAb activity (Richman et al., PNAS 2003) and co-receptor tropism (Whitcomb et al., 2007). The production of luciferase is dependent on virus entry and the completion of a single round of virus replication. Agents that inhibit pseudovirus entry or replication reduce luciferase activity in a dose-dependent manner, providing a quantitative measure of drug and antibody susceptibility. Over time, the PhenoSense® assay platform has been successfully adapted to evaluate vaccines and entry inhibitors that target a variety of enveloped viruses, including Orthomyxovirus (Influenza A & B), Paramyxovirus (RSV A & B), Filovirus (Ebola), and most recently Coronavirus (SARS CoV-2, SARS CoV, NL63).

As illustrated in FIG. 1, the measurement of nAb activity using the PhenoSense® SARS CoV-2 nAb Assay is performed by generating HIV-1 pseudovirions that express the SARS CoV-2 spike protein. The pseudovirions may be produced by transfecting cells (e.g., HEK293 cells) with an HIV-1 genomic vector and a SARS CoV-2 envelope expression vector that expresses the S protein (S-ORF) such that producer cells are generated that allow for the production of HIV pseudovirions that express the SARS CoV-2 S protein.

The assay also includes target cells that are produced by transfecting cells (e.g., HEK293 cells) with an angiotensin converting enzyme 2 (ACE-2) expression vector and a human airway transmembrane trypsin-like serine protease (TMPRSS) expression vector. ACE-2 is a receptor for SARS CoV and SARS CoV-2 (FIGS. 1 and 2). Thus, the target cells are susceptible to infection with the HIV pseudovirions that express the SARS CoV-2 S protein. Infection can be quantitated by the expression of luciferase (present in the pseudovirion).

To perform the assay, target cells are infected with the pseudovirions in the presence or absence of sera from the subject. Thus, upon infection of target cells that express both (ACE-2) and TMPRSS2, neutralizing antibody activity is measured by assessing the inhibition of luciferase activity in HEK293 target cells expressing the ACE2 receptor following pre-incubation of the pseudovirions with serial dilutions of the serum specimen.

Data can be displayed by plotting the percent inhibition of luciferase activity vs. log 10 reciprocal of the serum/plasma dilution and nAb titers are reported as the reciprocal of the serum dilution conferring 50% inhibition ($ID_{50}$) of pseudovirus infection. This can be expressed as follows: % Inhibition=100%−(((RLU(Vector+Sample+Diluent)−RLU (Background))/(RLU(Vector+Diluent)−RLU(Background)))×100%. The results of the PhenoSense SARS CoV-2 nAb can be reported as an $ID_{50}$ titer (1/Dilution) or qualitatively (positive, negative) based on a pre-defined dilution cutoff (e.g. >50% inhibition at 1:40 dilution). To insure that the measured nAb activity is SARS CoV-2 nAb specific, each test specimen is also assessed using a non-specific pseudovirus (specificity control) that expresses a non-reactive envelope protein of one or more unrelated viruses (e.g. avian influenza virus).

Example 2—Cotransfection of Target Cells with nAChR

Figure 3:
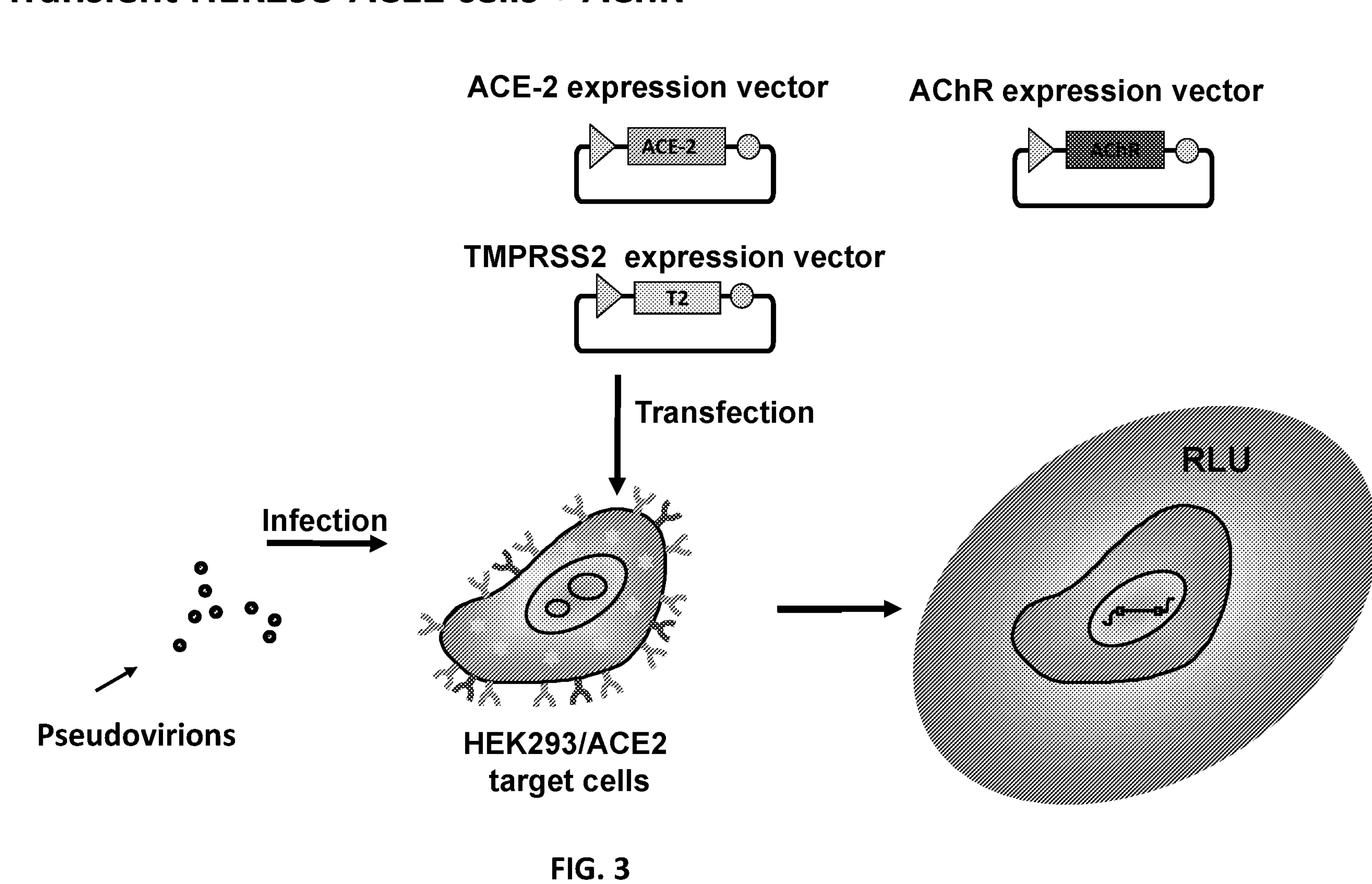
FIG. 3 depicts an example of in vitro target cells transfected with a SARS CoV-2 ACE-2 expression vector, a TMPRSS2 expression vector, and an AChR expression vector used to detect SARS-CoV-2 infection in accordance with an embodiment of the disclosure. ACE-2 refers to the SARS CoV and SARS CoV-2 receptor (angiotensin converting enzyme 2); TMPRSS2 refers to the human airway transmembrane trypsin-like serine protease; and AchR refers to the Cholinergic Receptor Nicotinic Alpha 7 Subunit (CHRNA7 or $\alpha7$ nAChR).
Figure 4:
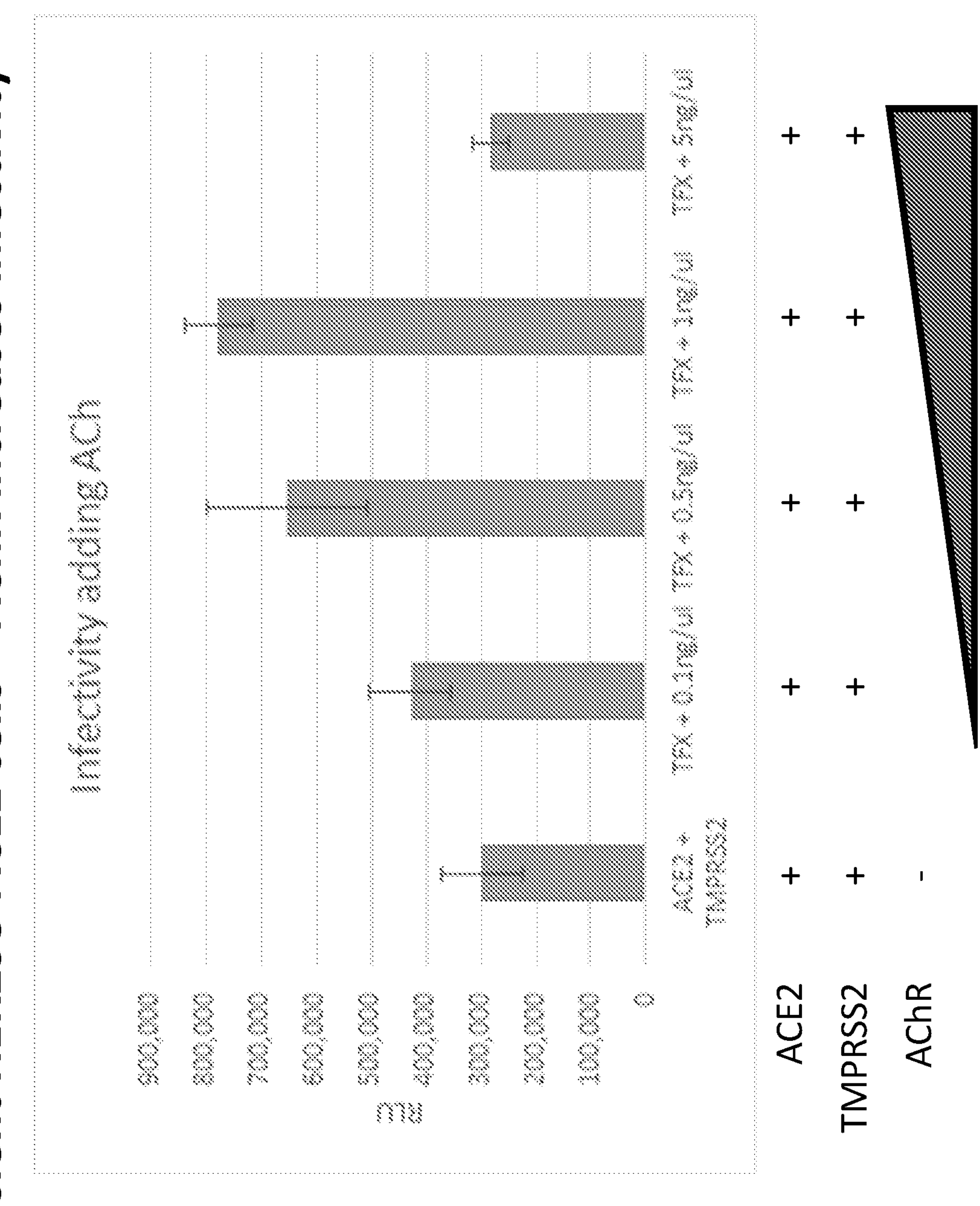
FIG. 4 shows that expression of nAChR can modulate SARS-CoV-2 infectivity in accordance with an embodiment of the disclosure.

Using the assay described in Example 1, it was determined that the α7 nicotinic acetylcholine receptor (nAChR) modulates infectivity of HIV pseudovirions that express the SARS CoV-2 S protein. In these experiments, the assay was performed as described in Example 1, with the additional step of transfecting the target cells with an AChR expression vector to express the α7 nAChR, along with ACE-2 and TMPRSS2 in target cells (FIG. 3). It was found that co-expression of the nAChR along with ACE-2 increased infectivity (as measured by increased luciferase activity) (FIG. 4).

Example 3—Embodiments

A1. A method to identify a compound that can modulate infection by a coronavirus comprising:

expressing an angiotensin-converting enzyme 2 receptor (ACE-2) and/or a nicotinic acetylcholine receptor (nAChR) receptor on a target cell;

contacting the target cell with a viral particle comprising at least a portion of the coronavirus spike protein in the absence and the presence of the compound; and measuring levels of infection of the target cell in order to determine infectivity of the viral particle in the presence or absence of the compound.

A2. The method of embodiment A1, wherein the coronavirus is SARS CoV-2.

A3. The method of embodiment A2, wherein the SARS CoV-2 is a variant, and wherein the variant is the Delta variant, Alpha variant, Beta variant, Gamma variant, Epsilon variant, Eta variant, Iota variant, Kappa variant, 1.617.3 variant, Mu variant, or Zeta variant.

A4. The method of embodiment A1, wherein the coronavirus is SARS CoV or NL63.

A5. The method of any one of embodiments A1-A4, wherein the viral particle is an HIV pseudovirion.

A6. The method of any one of embodiments A1-A5, wherein the nAChR is the α7 nAChR.

B1. A method to determine the efficacy of a compound to modulate the production of coronavirus neutralizing antibodies in a subject, comprising:

expressing an angiotensin-converting enzyme 2 receptor (ACE-2) and/or a nicotinic acetylcholine receptor (nAChR) receptor on a target cell;

contacting the target cell with a viral particle comprising at least a portion of the coronavirus spike protein, optionally from the subject, in the absence and the presence of: (i) a first sample obtained from the subject before treatment with the compound, and (ii) a second sample obtained from the subject after treatment with the compound, wherein the first and second samples contain antibodies; and measuring levels of infection of the target cell in order to determine infectivity of the viral particles in the presence in the presence of the first subject sample and the second subject sample in order to determine a change in the activity or amount of neutralizing antibodies in the subject's first and second samples, wherein a change in the activity or amount of neutralizing antibodies is detected as a change in infectivity of the viral particles.

B2. The method of embodiment B1, wherein the coronavirus is SARS CoV-2.

B3. The method of embodiment B2, wherein the SARS CoV-2 is a variant, and wherein the variant is the Delta variant, Alpha variant, Beta variant, Gamma variant, Epsilon variant, Eta variant, Iota variant, Kappa variant, 1.617.3 variant, Mu variant, or Zeta variant.

B4. The method of embodiment B1, wherein the coronavirus is SARS CoV or NL63.

B5. The method of any one of the previous or subsequent embodiments, wherein the viral particle is an HIV pseudovirion.

B6. The method any one of the previous or subsequent embodiments, wherein the nAChR is the α7 nAChR.

B7. The method of any one of the previous or subsequent embodiments, wherein the coronavirus spike protein is a coronavirus S protein.

B8. The method of any one of the previous or subsequent embodiments, wherein the indicator nucleic acid comprises an indicator gene.

B9. The method of any one of the previous or subsequent embodiments, wherein the indicator gene is a luciferase gene.

B10. The method of any one of the previous or subsequent embodiments, wherein the subject is or was infected with a coronavirus.

B11. The method of any one of the previous or subsequent embodiments, wherein the subject 20 is or was infected with severe acute respiratory syndrome coronavirus 2 (SARS-CoV-2).

B12. The method of any one of the previous or subsequent embodiments, wherein the subject is or was infected with SARS CoV or NL63.

B13. The method of any one of the previous or subsequent embodiments, wherein the producer cells and/or the target cells are mammalian cells.

B14. The method of any one of the previous or subsequent embodiments, wherein the producer cells and/or the target cells are human cells.

B15. The method of any one of the previous or subsequent embodiments, wherein the producer cells and/or the target cells are human embryonic kidney cells.

B16. The method of any one of the previous or subsequent embodiments, wherein the human embryonic kidney cells are 293 (HEK293) cells.

B17. The method of any one of the previous or subsequent embodiments, wherein the sample is serum or plasma.

B18. The method of any one of the previous or subsequent embodiments, wherein the target cell further expresses human airway transmembrane trypsin-like serine protease (TMPRSS2).

B19. The method any one of the previous or subsequent embodiments, wherein the compound is an nAChR antagonist.

C1. A method to identify a compound that can modulate coronavirus infection, comprising:

(a) transfecting into a producer cell:

i) a nucleic acid encoding a coronavirus spike protein or a portion thereof, and ii) a genomic viral expression vector comprising sequences from a second virus that is not a coronavirus and that comprises an indicator nucleic acid that produces a detectable signal;

(b) incubating the transfected producer cell under conditions such that pseudovirions that comprise the coronavirus spike protein or a portion thereof are generated;

(c) contacting the pseudovirions of step (b) with a target cell under conditions such that the pseudovirions infect the target cell and in the presence or absence of the compound, wherein the target cell expresses an angiotensin-converting enzyme 2 receptor (ACE-2) and/or a nicotinic acetylcholine receptor (nAChR); and (d) measuring the amount of the detectable signal produced by the target cell in order to determine infectivity of the viral particles in the presence or absence of the compound.

C2. The method of embodiment C1, wherein the coronavirus is SARS CoV-2.

C3. The method of embodiment C2, wherein the SARS CoV-2 is a variant, and wherein the variant is the Delta variant, Alpha variant, Beta variant, Gamma variant, Epsilon variant, Eta variant, Iota variant, Kappa variant, 1.617.3 variant, Mu variant, or Zeta variant.

C4. The method of embodiment C1, wherein the coronavirus is SARS CoV or NL63.

C5. The method of any one of embodiments C1-$C_4$, wherein the nAChR is the α7 nAChR.

C6. The method of any one of embodiments C1-C5, wherein the second virus is HIV or a genetically modified HIV.

C7. The method of any one of the previous embodiments, wherein the compound is an nAchR antagonist.

D1. A method to determine the efficacy of a compound to modulate the production of coronavirus neutralizing antibodies in a subject, comprising:
- (a) transfecting into a producer cell:
  - i) a nucleic acid encoding a coronavirus spike protein or a portion thereof, optionally from the subject, and
  - ii) a genomic viral expression vector comprising sequences from a second virus that is not a coronavirus and that comprises an indicator nucleic acid that produces a detectable signal;
- (b) incubating the transfected producer cell under conditions such that the producer cell produces pseudovirions that comprise the coronavirus spike protein or a portion thereof;
- (c) contacting the pseudovirions of step (b) with a target cell in the presence or absence of: (i) a first sample obtained from the subject before treatment with the compound, and (ii) a second sample obtained from the subject after treatment with the compound, and wherein the target cell expresses an angiotensin-converting enzyme 2 receptor (ACE-2) and/or a nicotinic acetylcholine receptor (nAChR) under conditions such that the pseudovirions infect the target cell;
- (d) measuring the amount of the detectable signal produced by the target cell in the presence of the first subject sample and the second subject sample in order to determine a change in the activity or amount of neutralizing antibodies in the subject's first and second samples, wherein a change in the activity or amount of neutralizing antibodies is detected as a change in infectivity of the viral particles.

D2. The method of embodiment D1, wherein the coronavirus is SARS CoV-2.

D3. The method of embodiment D2, wherein the SARS CoV-2 is a variant, and wherein the variant is the Delta variant, Alpha variant, Beta variant, Gamma variant, Epsilon variant, Eta variant, Iota variant, Kappa variant, 1.617.3 variant, Mu variant, or Zeta variant.

D4. The method of embodiment D1, wherein the coronavirus is SARS CoV or NL63.

D5. The method of any one of embodiments D1-D4, wherein the nAChR is the α7 nAChR.

D6. The method of any one of embodiments D1-D5, wherein the second virus is HIV or a genetically modified HIV.

D7. The method of any one of the previous or subsequent embodiments, wherein the compound is an nAchR antagonist.

E1. A system comprising a station and/or genetically modified cells for performing any of the steps of any of the previous embodiments or use any one of the compositions of any of the subsequent embodiments.

F1. A computer-program product tangibly embodied in a non-transitory machine-readable storage medium, including instructions configured to perform any of the steps of the methods of any of the previous embodiments, or use any one of the compositions of any of the subsequent embodiments, or run any part of the system of embodiment E1.

G1. A composition for the detection of a compound that can modulate coronavirus (e.g., SARS CoV-2) infectivity.

G2. The composition of embodiment G1, wherein the coronavirus is SARS CoV-2.

G3. The composition of embodiment G2, wherein the SARS CoV-2 is a variant, and wherein the variant is the Delta variant, Alpha variant, Beta variant, Gamma variant, Epsilon variant, Eta variant, Iota variant, Kappa variant, 1.617.3 variant, Mu variant, or Zeta variant.

G4. The composition of embodiment G1, wherein the coronavirus is SARS CoV or NL63.

G5. The composition of any one of the previous or subsequent embodiments, comprising a cell that has been genetically modified to be either a producer cell or a target cell.

G6. The composition of any one of the previous or subsequent embodiments, comprising a first cell that has been genetically modified to be a target cell that expresses an angiotensin-converting enzyme 2 receptor (ACE-2) and/or a nicotinic acetylcholine receptor (nAChR) receptor.

G7. The composition of any one of the previous or subsequent embodiments, wherein the target cell is genetically modified to also express human airway transmembrane trypsin-like serine protease (TMPRSS2).

G8. The composition of any one of the previous or subsequent embodiments comprising a producer cell.

G9. The composition of any one of the previous or subsequent embodiments, wherein the producer cell is a genetically modified second cell that expresses: i) a coronavirus spike protein or a portion thereof, and ii) a second virus, or a portion thereof, that is not a coronavirus and that comprises an indicator nucleic acid that produces a detectable signal.

G10. The composition of any one of the previous or subsequent embodiments, wherein the producer cell generates pseudovirions that comprise the coronavirus spike protein or a portion thereof.

G11. The composition of any one of the previous or subsequent embodiments, wherein the coronavirus spike protein is a coronavirus S protein.

G12. The composition of any one of the previous or subsequent embodiments, wherein the S protein is from a subject infected with a coronavirus.

G13. The composition of any one of the previous or subsequent embodiments, wherein the subject is infected with severe acute respiratory syndrome coronavirus 2 (SARS-CoV-2).

G14. The composition of any one of the previous or subsequent embodiments, wherein the subject is infected with SARS CoV and/or NL63.

G15. The composition of any one of the previous or subsequent embodiments, wherein the second virus is HIV or a genetically modified HIV.

G16. The composition of any one of the previous or subsequent embodiments, wherein the nAChR is the α7 nAChR.

G17. The composition of any one of the previous or subsequent embodiments, wherein the indicator nucleic acid comprises an indicator gene.

G18. The composition of any one of the previous or subsequent embodiments, wherein the indicator gene is a luciferase gene.

G19. The composition of any one of the previous or subsequent embodiments, wherein the producer cells and/or the target cells are mammalian cells.

G20. The composition of any one of the previous or subsequent embodiments, wherein the producer cells and/or the target cells are human cells.

G21. The composition of any one of the previous or subsequent embodiments, wherein the producer cells and/or the target cells are human embryonic kidney (HEK) cells.

G22. The composition of any one of the previous or subsequent embodiments, wherein the human embryonic kidney cells are HEK 293 cells.

G23. The composition of any of the previous embodiments, wherein the compound is an nAchR antagonist.

H1. A compound identified using any one of the previous embodiments.

I1. A method of treatment comprising using the compound of H1 to reduce or prevent symptoms of a SARS CoV-2 infection.

I2. A method of treatment comprising using the compound of H1 to reduce or prevent symptoms of a SARS CoV infection and/or an NL63 infection.

J1. A method of treatment, comprising administering to a subject or a patient an inhibitor that interferes with the binding or interaction of SARS CoV-2 in the subject or patient with an AchR receptor.

J2. A method of treatment, comprising administering to a subject or a patient an inhibitor that interferes with the binding or interaction of SARS CoV or NL63 in the subject or patient with an AchR receptor.

That which is claimed is:

1. A method to identify a compound that can modulate infection by a coronavirus comprising:

obtaining a target cell, wherein the target cell is engineered to express an angiotensin-converting enzyme 2 receptor (ACE-2), a Transmembrane trypsin like serine protease (TMPRSS2), and a nicotinic acetylcholine receptor (nAChR);

contacting the target cell with a viral particle comprising at least a portion of a coronavirus spike protein in the absence and the presence of the compound; and measuring levels of infection of the target cell in order to determine infectivity of the viral particle in the presence or absence of the compound.

2. The method of claim 1, wherein the coronavirus is severe acute respiratory syndrome coronavirus 2 (SARS COV-2).

3. The method of claim 2, wherein the SARS COV-2 is a variant, and wherein the variant is a Delta variant, Alpha variant, Beta variant, Gamma variant, Epsilon variant, Eta variant, Iota variant, Kappa variant, 1.617.3 variant, Mu variant, or Zeta variant.

4. The method of claim 1, wherein the coronavirus is severe acute respiratory syndrome coronavirus (SARS COV) or seasonal coronavirus NL63.

5. The method of claim 1 wherein the viral particle is an HIV pseudovirion.

6. The method of claim 1, wherein the nAChR is a $\alpha 7$ nAChR.

7. A method to determine an efficacy of a compound to modulate the production of coronavirus neutralizing antibodies in a subject, comprising:

obtaining a target cell, wherein the target cell is engineered to express an angiotensin-converting enzyme 2 receptor (ACE-2), a Transmembrane trypsin like serine protease (TMPRSS2), and a nicotinic acetylcholine receptor (nAChR);

contacting the target cell with a viral particle comprising at least a portion of a coronavirus spike protein from the subject in the absence and the presence of: (i) a first sample obtained from the subject before treatment with the compound, and (ii) a second sample obtained from the subject after treatment with the compound, wherein the first and second samples comprise antibodies; and measuring levels of infection of the target cell in order to determine infectivity of the viral particles in the presence of the first subject sample and the second subject sample in order to determine a change in the activity or amount of neutralizing antibodies in the subject's first and second samples, wherein a change in the activity or amount of neutralizing antibodies is detected as a change in infectivity of the viral particles.

8. The method of claim 7, wherein the coronavirus is severe acute respiratory syndrome coronavirus 2 (SARS COV-2).

9. The method of claim 8, wherein the SARS COV-2 is a variant, and wherein the variant is a Delta variant, Alpha variant, Beta variant, Gamma variant, Epsilon variant, Eta variant, Iota variant, Kappa variant, 1.617.3 variant, Mu variant, or Zeta variant.

10. The method of claim 7, wherein the coronavirus is severe acute respiratory syndrome coronavirus (SARS COV) or seasonal coronavirus NL63.

11. The method of claim 7, wherein the viral particle is an HIV pseudovirion.

12. The method of claim 7, wherein the nAChR is an $\alpha 7$ nAChR.

13. A method to identify a compound that can modulate coronavirus infection, comprising:

(a) transfecting into a producer cell:

i) a nucleic acid encoding a coronavirus spike protein or a portion thereof, and ii) a genomic viral expression vector comprising sequences from a virus that is not a coronavirus and that comprises an indicator nucleic acid that produces a detectable signal;

(b) incubating the transfected producer cell under conditions such that pseudovirions that comprise the coronavirus spike protein or a portion thereof are generated;

(c) contacting the pseudovirions of step (b) with a target cell under conditions such that the pseudovirions infect the target cell and in the presence or absence of the compound, wherein the target cell expresses an angiotensin-converting enzyme 2 receptor (ACE-2), a Transmembrane trypsin like serine protease (TMPRSSS2), and a nicotinic acetylcholine receptor (nAChR); and (d) measuring the amount of the detectable signal produced by the target cell in order to determine infectivity of the in the presence or absence of the compound.

14. The method of claim 13, wherein the coronavirus is severe acute respiratory syndrome coronavirus 2 (SARS CoV-2).

15. The method of claim 14, wherein the SARS CoV-2 is a variant, and wherein the variant is a Delta variant, Alpha variant, Beta variant, Gamma variant, Epsilon variant, Eta variant, Iota variant, Kappa variant, 1.617.3 variant, Mu variant, or Zeta variant.

16. The method of claim 13, wherein the coronavirus is severe acute respiratory syndrome coronavirus (SARS CoV) or seasonal coronavirus NL63.

17. The method of claim 13, wherein the nAChR is an α7 nAChR.

18. The method of claim 13, wherein the virus of step a)ii) is HIV or a genetically modified HIV.

19. The method of claim 13, wherein the compound is an nAChR antagonist.

20. The method of claim 13, wherein step (c) is performed on (i) a first sample obtained from a subject before treatment with the compound, and (ii) a second sample obtained from the subject after treatment with the compound; and wherein step (d) comprises measuring the amount of the detectable signal produced by the target cell in the presence of the first sample and the second sample in order to determine a change in the activity or amount of neutralizing antibodies in the first and second samples, wherein a change in the activity or amount of neutralizing antibodies is detected as a change in infectivity of the pseudovirions.

* * * * *